United States Patent
Dai et al.

(10) Patent No.: US 9,012,676 B2
(45) Date of Patent: Apr. 21, 2015

(54) PROCESSES FOR PRODUCING ARYL CARBAMATES, ISOCYNATES AND POLYUREAS USING DIARYL CARBONATE

(75) Inventors: Shenghong A. Dai, Taichung (TW); Hsueh-Yung Chen, Taichung (TW); Chao-Hsing Lin, Taichung (TW); Chun-Ying Huang, Taichung (TW); Wen-Chen Pan, Taichung (TW)

(73) Assignees: Great Eastern Resins Industrial Co., Ltd., Taiwan (CN); National Chung Hsing University, Taiwan (CN)

( * ) Notice: Subject to any disclaimer, the term of this patent is extended or adjusted under 35 U.S.C. 154(b) by 0 days.

(21) Appl. No.: 13/239,664

(22) Filed: Sep. 22, 2011

(65) Prior Publication Data

US 2013/0079542 A1    Mar. 28, 2013

(51) Int. Cl.
| | |
|---|---|
| C07C 261/00 | (2006.01) |
| C07C 269/00 | (2006.01) |
| C07C 271/00 | (2006.01) |
| C07C 263/04 | (2006.01) |
| C07C 269/04 | (2006.01) |
| C08G 18/76 | (2006.01) |
| C08G 71/02 | (2006.01) |

(52) U.S. Cl.
CPC ............. *C07C 263/04* (2013.01); *C07C 269/04* (2013.01); *C08G 18/7671* (2013.01); *C08G 71/02* (2013.01)

(58) Field of Classification Search
USPC ........ 560/3, 11, 13, 17, 29, 32, 115, 132, 138
See application file for complete search history.

(56) References Cited

U.S. PATENT DOCUMENTS

| | | | |
|---|---|---|---|
| 3,895,094 A | | 7/1975 | Carter et al. |
| 4,487,713 A | * | 12/1984 | Spohn ........................... 560/345 |
| 4,547,322 A | | 10/1985 | Fukuoka et al. |
| 6,143,917 A | * | 11/2000 | Harada et al. ................... 560/32 |
| 6,781,010 B1 | | 8/2004 | Mason |
| 7,122,697 B2 | | 10/2006 | Yoshida et al. |
| 2003/0078450 A1 | * | 4/2003 | Kocher et al. ................... 560/26 |
| 2011/0054211 A1 | | 3/2011 | Shinohata et al. |

OTHER PUBLICATIONS

Noboru Yamazaki et al., *The Reaction of Diphenyl Carbonate with Amines and Its Application to Polymer Synthesis*, J. Polymer. Sci. Polym. Chem., 1979, 17, 835-841.
Steffen Maier et al., *Carbonylbiscaprolactam: A Versatile Reagent for Organic Synthesis and Isocyanate-Free Urethane Chemistry*, Angew. Chem. 2003, 42, 5094-5097.
Steffen Maier et al., *Isocyanate-Free Route to Caprolactam-Blocked Oligomeric Isocyanates via Carbonylbiscaprolactam-(CBC-)Mediated End Group Conversion*, Macromolecules 2003, 36, 4727.
Ron M. Versteegen et al., *Synthesis and Characterization of Segmented Copoly(ether urea)s with Uniform Hard Segments*, Macromolecules 2005, 38, 3176-3184.
Ron M. Versteegen et al., *Properties and Morphology of Segmented Copoly(ether urea)s with Uniform Hard Segments*, Macromolecules 2006, 39, 772-783.
P. Deepa et al., *Solvent-Induced Self-Organization Approach for Polymeric Architectures of Micropores, Hexagons and Spheres Based on Polyurethanes Prepared via Novel Melt Transurethane Methodology*, J. Polym. Sci., Part A: Polym. Chem. 2007, 45, 2351-2366.
Shenghong A. Dai, *Green Chemistry Approach to MDI and Polyurea*, Paper published in Polymer Cross-Strait Seminar, Oct. 11, 2010.

* cited by examiner

*Primary Examiner* — Brandon Fetterolf
*Assistant Examiner* — Blaine G Doletski
(74) *Attorney, Agent, or Firm* — Drinker Biddle & Reath LLP

(57) ABSTRACT

A preparation of aryl carbamates can be achieved readily by carbonylation of an aromatic polyamine compound with diphenyl carbonate (DPC) using a combination of an organic acid and a tertiary amine as a catalyst. Aryl carbamate can be converted into 4,4'-diphenylmethane diisocyanate (MDI) by heating it at about 200 to about 230° C. in a non-polar solvent containing inhibitor such as benzoyl chloride. In another application, trans-ureation of biscarbamates with an amine or mixed amines is found to be extremely facile in a polar solvent such as dimethyl sulfoxide (DMSO) and tetramethylene sulfone (TMS) in absence of any catalyst to make polyurea polymers of high molecular weights. Thus, efficient green-chemistry processes based on biscarbamates in making isocyanate products as well as urea prepolymers, urea elastomers and urea plastics have been developed in all in excellent yields without using reactive phosgene or 4,4'-diphenylmethane diisocyanate separately in the trans-ureation polymerizations.

16 Claims, 1 Drawing Sheet

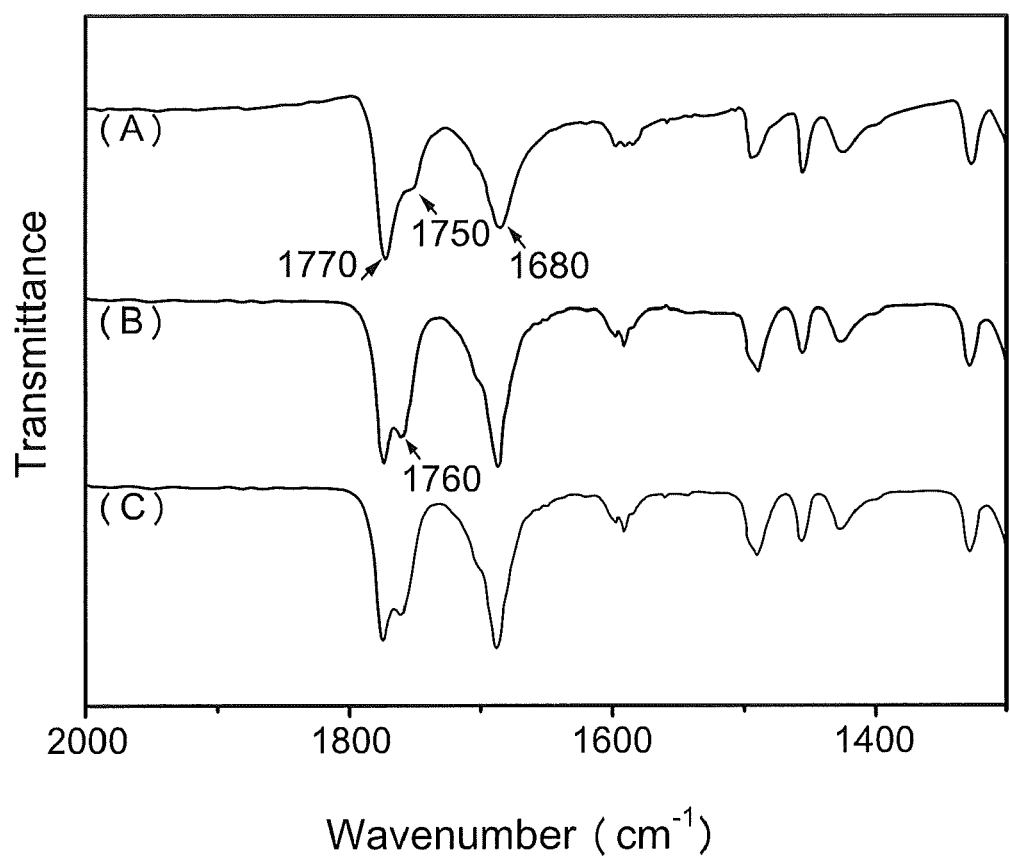

PROCESSES FOR PRODUCING ARYL CARBAMATES, ISOCYNATES AND POLYUREAS USING DIARYL CARBONATE

BACKGROUND OF THE INVENTION

1. Field of the Invention

The present invention relates generally to a process for producing an aryl carbamate from an aromatic polyamine with a diaryl carbonate and to a process for producing aryl isocynates and polyureas from the obtained diaryl carbamates.

2. Description of the Related Art

Organic isocyanates have widespread industrial applications. The isocyanates manufactured in the largest volume are the organic di- and polyarylisocyanates employed in polymer manufacture, particularly in the production of polyurethanes, polyurethane/ureas, polyisocyanurates, and related polymers.

Both aryl as well as aliphatic polyisocyanates are useful. Aryl diisocyanates such as 2,4- and 2,6-toluene diisocyanate (TDI) and 4,4'-diphenylmethane diisocyanate (MDI) dominate isocyanate production because of cost and performance considerations, their reactivity profiles, and their utility in polyurethane molded and slabstock foam productions. However, the production process of MDI and TDI, which have enjoyed an annual gross production of over 3.5 million tons globally, are still being practiced by the phosgene process. Because of toxicity of phosgene used and corrosive hydrogen chloride generated in the production, green and non-phosgene processes of producing MDI and TDI has been intensely sought for the last thirty years to better comply with public demand and work-place safety.

In the developments of non-phosgene processes for MDI and TDI, the most sought-after substitutes of phosgene in the research have been urea/alcohols, di-substituted carbonates and carbon monoxide as the carbonylation reagents for making biscarbamates as the precursors to isocyanates. For example, Olin discloses a process of converting nitro groups into isocyanates with carbon monoxide in the presence of platinum and rhodium as catalysts, but the process has not been accepted by the industry, because of the low yield of isocyanates and harsh reaction conditions of high temperature and pressure, and expensive catalysts recovery problems.

Essentially since Olin's process, most if not all of the non-phosgene routes involve a carbonylation step to convert diamine- or dinitro-groups into their corresponding biscarbamates. Then, MDI and TDI are generated by thermolysis of the respective biscarbamates to liberate the isocyanate groups from the alcohols.

For example, U.S. Pat. No. 3,895,094 (ARCO process) discloses a process for the manufacture of a methyl phenyl carbamate by reacting a nitrobenzene, methanol, and carbon monoxide in the presence of a catalyst of selenium, which is then reacted with formaldehyde under acidic condensation to form N,N'-dimethyl-4,4'-methylenediphenylene-biscarbamate. N,N'-dimethyl-4,4'-methylenediphenylene-biscarbamate is then subjected to thermolysis to form 4,4'-methylenediphenylene diisocyanate (MDI). Nevertheless, the catalyst, selenium, applied in this process is toxic and therefore is not good to the environment; and the temperature for the thermolysis process is very high (240 to 260° C.). In addition, the Se catalyst is difficult to be re-cycled and there are many by-products produced during the thermolysis process. Therefore, this process has not been accepted in industry.

Later in 1978, U.S. Pat. No. 4,547,322 (Asahi process) modified the ARCO process and used palladium (Pd) and sodium iodide as the catalysts instead. This process used aniline, carbon monoxide, and ethanol as reactants to form ethyl phenyl carbamates, which was then reacted with formaldehyde under acidic catalyzed condensation to form N,N'-diethyl-4,4'-methylenediphenylene biscarbamate. N,N'-diethyl-4,4'-methylenediphenylene biscarbamates was then subjected to thermolysis to form 4,4'-methylenediphenylene diisocyanate. Nevertheless, the catalyst, palladium, applied in this carbonylation process is very expensive and difficult to recycle. Moreover, the thermolysis temperature is still high (about 250° C.). Therefore, this process is not economically attractive.

Given the disadvantages described above, bis-N,N'-dimethyl-4,4'-methylenediphenylene biscarbamates (4,4'-DM-MDC) or N,N'-diethyl-4,4'-methylenediphenylene-biscarbamate (4,4'-DE-MDC) have not been implemented practically for MDI production, though they were touted as the most important precursors for non-phosgene synthesis of MDI since 1980s.

Yamazaki's study showed a carbonylation reaction of 4,4'-methylenedianiline (4,4'-MDA) with diphenyl carbonate (DPC) producing 4,4'-DP-MDC in a yield of 68% with 2-hydroxypyridine as the catalyst (*J. Polymer. Sci. Polym. Chem.* 1979, 17, 835). More recently, Harada (U.S. Pat. No. 6,143,917) found that the yield of N,N'-diphenyl-4,4'-methylenediphenylene biscarbamate (4,4'-DP-MDC) could be enhanced by treating 4,4'-MDA with a diphenyl carbonate in the presence of carboxylic acids such as pivalic acid or benzoic acid as the catalyst at a temperature of −30° C. to 200° C. The carbonylation reaction scheme of MDA is as follows.

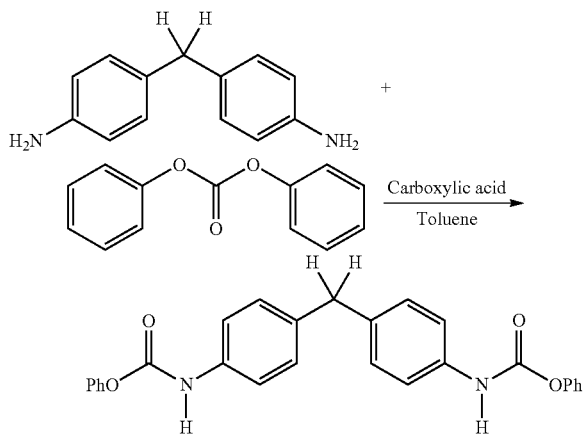

Under later conditions, high conversion (>90%) with high purity of 4,4'-DP-MDC was found achievable in toluene.

4,4'-DP-MDC produced above can be then subjected to thermolysis to form 4,4'-MDI. At present, the thermolysis process can be carried out in a gaseous state or liquid state. The gaseous reaction is usually performed at a temperature of 400 to 600° C. in the presence of a Lewis acid as catalyst, and the liquid state reaction is usually performed at a temperature of 80 to 300° C. Since the gaseous reaction requires very high processing temperature and the yield of 4,4'-MDI is low, the liquid state process is more frequently used in undergoing the thermolysis process to form 4,4'-MDI.

Polyurea and polyurea elastomers have been known to possess many outstanding mechanical properties. Currently, important polyurea commercial markets are in automotive and construction applications with familiar finished products such as bumpers, fascia, waterproofing linings, thermal insulation materials, industrial flooring and sports facilities. However, due to high reaction rates of diisocyanates such as methylenediphenylene diisocyanates (MDI) and diamines, the synthesis and processing of polyurea and polyurea elastomers have been heavily dependent upon the assistance of reaction injection molding (RIM)-machine or high-pressure mixing equipments. Synthesis of polyureas in bulk through more controllable step-wise manners has rarely been reported and will be highly prized for polyurea formulation and products development. If the synthesis of polyurea can completely avoid using diisocyanates such as MDI or TDI as the raw materials, it would become even more attractive because of elimination of highly toxic and reactive diisocyanates in the overall synthetic scheme.

Therefore, in a non-isocyanate route (NIR) to polyurea, the approach based on MDI-biscarbamates seems promising because no high-temperature condition seems required through trans-esterification or trans-ureation. In fact, several attempts have tried to use carbamates, or biscarbamates directly as precursors for polyurethane (PU) and polyurea synthesis bypassing isolation of diisocyanate completely (*J. Polym. Sci. Polym. Chem.* 1979, 17, 835). A model rapid and selective trans-ureation reaction scheme of synthesis of 4,4'-diphenylmethanbis-[(2-hydroxyethyl)urea] has been achieved in dimethyl sulfoxide (DMSO) solution as exemplified as follows where the urea derivative was formed in a high selective yield. However, no report of trans-ureation polymerization of N,N'-diphenyl-4,4'-methylenediphenylene biscarbamate (4,4'-DP-MDC) has been reported under DMSO or tetramethylene sulfone (TMS) prior to the study.

diamines with new intermediates. For example, Meijer uses di-tert-butyl tricarbonate and diamine terminated poly(tetrahydrofuran) serving as raw materials for making thermoplastic elastomers (TPEs) of urea segmented block copolymers (*Macromolecules* 2005, 38, 3176; *Macromolecules* 2006, 39, 772). Another approach for preparing polyureas without isocyanate chemistry was reported in Mtilhaupt's studies where a carbonyl biscaprolactam served as a non-halogen building block that could convert the terminal amine-groups of functional polymers into the corresponding caprolactam-blocked isocyanates (*Angew. Chem.* 2003, 42, 5094; *Macromolecules* 2003, 36, 4727). Although these approaches appear to be non-isocyanate processes to polyureas in nature, high cost of di-tert-butyl tricarbonate and carbonyl biscaprolactam seems limiting their wide-spread applications.

BRIEF SUMMARY OF THE INVENTION

The present invention provides a process for facilitating the production of an aryl carbamate, comprising a reaction of a diaryl carbonate with an aromatic polyamine compound in the presence of a combination of at least one carboxylic acid and a tertiary amine as carbonylation catalyst combination.

In the process of the production of an aryl carbamate, after the reaction is completed, the resulted mixture may be cooled to a room temperature to cause the targeted aryl carbamates to precipitate from the mixture, and the precipitated aryl carbamate may be isolated and collected from the mixture in substantial pure form for further use in making isocyanates or polyureas.

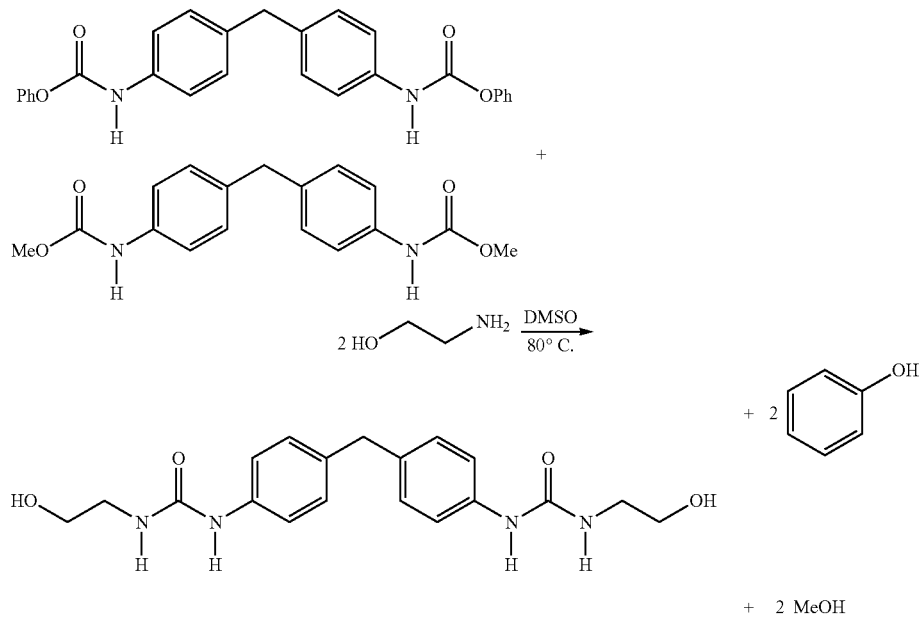

Metal or Lewis acid catalyzed trans-esterifications of diols and diamines with biscarbamates also have been studied in recent reports with some successes (*J. Polym. Sci., Part A: Polym. Chem.* 2007, 45, 2351) but the use of metal catalysts in the process is neither economically nor environmentally acceptable. In addition, the molecular weights of PUs made through those trans-esterification processes are generally not high.

Recently, other non-isocyanate synthesis of making polyurea and polyurethanes has been explored with reaction of Therefore, the present invention also provides a process for facilitating the production of isocyanates, comprising applying a thermo decomposition reaction to the aryl polycarbamates obtained by the process mentioned above in the presence of an inhibitor and a non-polar solvent.

The present invention also provides a process for facilitating the production of a polyurea, comprising a reaction of the aryl carbamate obtained by the process mentioned above with an amine compound or mixtures thereof in the presence of a polar solvent.

According to the present invention, aryl carbamates can be effectively produced and isolated at lower reaction temperature from aromatic polyamines. Furthermore, isocynates can be effectively generated by thermolysis of the aryl carbamates produced according to the present invention in the presence of an inhibitor and a non-polar solvent.

In addition, according to the present invention, the transureation of the aryl carbamates produced according to the present invention with varieties of polyamines and polyamine mixtures in a polar solvent is capable of producing high molecular weight polyureas greater than 50,000 with adequate mechanical properties.

Every aspect and every embodiment of the invention are disclosed herein is meant to be combined with all the other disclosed aspects and embodiments of the invention individually and in all possible combinations thereof.

BRIEF DESCRIPTION OF THE DRAWING

FIG. 1 shows (carbonyl regions of) infrared spectra monitoring carbonylation of 4,4'-methylene diphenyl dicarbamate (4,4'-DP-MDC).

DETAILED DESCRIPTION OF THE INVENTION

In the specification and claims, the singular forms "a," "an," and "the" include the plural unless the context clearly dictates otherwise. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

According to the present invention, an aryl carbamate is produced by reaction of a diaryl carbonate with an aromatic polyamine compound in the presence of the carbonylation catalyst comprising at least one carboxylic acid and a tertiary amine. No metal catalyst is involved in this invention.

The diaryl carbonate used in the process according to the present invention is a compound represented by the following formula (1):

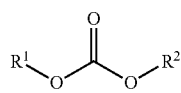

(1)

in which $R^1$ and $R^2$ represent an aromatic group having 6 to 20 carbon atoms, and preferably an aromatic group having 6 to 12 carbon atoms. $R^1$ and $R^2$ can be the aromatic compounds with their rings substituted by one or more substituents (aliphatic of cyclo-aliphatic) or non-substituted. In the case where the aryl groups have two or more substituents, these substituents can be the same as each other or different from each other.

The substituents, which can be contained in $R^1$ and $R^2$, are preferably selected from alkyl or cycloalkyl having 1 to 12 carbon atoms, for example, methyl, ethyl, propyl, and butyl; aralkyl having 7 to 15 carbon atoms, for example, benzyl and phenethyl; aryl having 6 to 14 carbon atoms, for example, phenyl and tolyl; alkoxy having 1 to 12 carbon atoms, for example, methoxy, ethoxy, propoxy, butoxy, and trifluoromethoxy; thioalkoxy having 1 to 12 carbon atoms, for example, thiomethoxy and thioethoxy; aryloxy having 6 to 14 carbon atoms, for example, a phenoxy; halogen, for example, fluorine, chlorine, and bromine; a nitro group; a hydroxyl; a cyano group; and dialkylamino groups, for example, a dimethylamino group.

The substituted and unsubstituted $R^1$ and $R^2$ include, for example, phenyl, naphthyl, anthranyl, tolyl, xylyl, ethylphenyl, propylphenyl, octylphenyl, nonylphenyl, dodecylphenyl, biphenyl, methoxyphenyl, chlorophenyl, dichlorophenyl, trichlorophenyl, pentachlorophenyl, bromophenyl, dibromophenyl, tribromophenyl, pentabromophenyl, nitrophenyl, dinitrophenyl, hydroxyphenyl, cyanophenyl, and dimethylaminophenyl.

Also, these aryl groups include o-, m-, and p-isomers, and the substituents attached to the aryl include n-, iso-, sec-, and tert-isomers.

Specifically, the diaryl carbonates having the same unsubstituted aryl groups as each other can be selected from, but not limited to, diphenyl carbonate, di-1-naphthyl carbonate, di-2-naphthyl carbonate and di-9-anthryl carbonate.

The diaryl carbonates having the same aryl groups as each other and each substituted with at least one alkyl group can be selected from, but not limited to, bis(2-tolyl)carbonate and bis[4-{tert-butyl}phenyl]carbonate.

The diaryl carbonates having the same aryl groups as each other and respectively substituted with at least one aryl group can include, but not limited to, bis(4-biphenylphenyl)carbonate.

The diaryl carbonates having the same aryl groups as each other and each substituted with at least one alkoxy group can be selected from, but not limited to, bis(2-methoxyphenyl) carbonate and bis(3-butoxyphenyl)carbonate.

The diaryl carbonates having the same aryl groups as each other and each substituted with at least one halogen atom can be selected from, but not limited to, bis(2-chlorophenyl)carbonate, bis(2,4-dichlorophenyl)carbonate, and bis(2,4,6-trichlorophenyl)carbonate.

The diaryl carbonates having the same aryl groups as each other and each substituted with at least one nitro group can be selected from, but not limited to, bis(2-nitrophenyl)carbonate and bis(2,4-dinitrophenyl)carbonate.

The diaryl carbonates having an unsubstituted aryl group and an aryl group substituted with at least one alkyl can be selected from, but not limited to, 3-tolylphenyl carbonate and 4-tolylphenyl carbonate.

The diaryl carbonates having an unsubstituted aryl group and an aryl group substituted with at least one aralkyl can include, but not limited to, 4-benzylphenyl(phenyl)carbonate.

The diaryl carbonates having an unsubstituted aryl group and an aryl group substituted with at least one alkoxy group can be selected from, but not limited to, 4-methoxyphenylphenyl carbonate and 4-ethoxy-1-naphthalenylphenyl carbonate.

The diaryl carbonates having an unsubstituted aryl group and an aryl group substituted with at least one thioalkoxy group can be selected from, but not limited to, 4-methylthiophenylphenyl carbonate.

The diaryl carbonates having an unsubstituted aryl group and an aryl group substituted with at least one aryloxy can include, but not limited to, 4-phenoxyphenylphenyl carbonate.

The diaryl carbonates having an unsubstituted aryl group and an aryl group substituted with at least one halogen atom can be selected from, but not limited to, 2-chlorophenylphenyl carbonate and 4-chlorophenylphenyl carbonate.

The diaryl carbonates having an unsubstituted aryl group and an aryl group substituted with at least one nitro group can be selected from, but not limited to, 3-nitrophenylphenyl carbonate and 2,4-dinitrophenylphenyl carbonate.

The diaryl carbonates having an unsubstituted aryl group and an aryl group substituted with at least one hydroxyl group can be selected from, but not limited to, 3-hydroxyphenylphenyl carbonate and 4-hydroxyphenylphenyl carbonate.

The other diaryl carbonates usable for the process of the present invention include, for example, 4-methoxypheenyl-4'-nitrophenyl carbonate, 4-cyanophenyl-4'-nitrophenyl carbonate, 4-thiomethoxyphenyl-4'-nitrophenyl carbonate, 2-chlorophenyl-4'-nitrophenyl carbonate, 2-dimethylaminophenylphenyl carbonate, 2-bromo-4-cyano-6-nitrophenylphenyl carbonate, and pentabromophenyl-2',4',6'-tribromophenyl carbonate.

Among the diary carbonates mentioned above, diphenyl carbonate, bis(2-tolyl)carbonate, bis(4-chlorophenyl)carbonate, bis(4-nitrophenyl)carbonate, and bis(3,5-dimethoxyphenyl)carbonate are preferably used, and diphenyl carbonate is more preferably used.

The aromatic polyamine compound used in the process according to the present invention is a compound represented by the following formula (2):

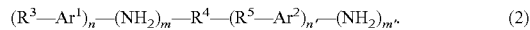

$$(R^3-Ar^1)_n-(NH_2)_m-R^4-(R^5-Ar^2)_{n'}-(NH_2)_{m'}. \quad (2)$$

in which $Ar^1$ and $Ar^2$ independently represent a group selected from the group consisting of simple phenyl group or aliphatic substituted phenyl compounds with an aliphatic substitution groups of having 1 to 20 carbon atoms and an aromatic group having 6 to 26 carbon atoms, m and m' represent an integer of from 1 to 10, and n and n' represent an integer of from 0 to 3 wherein $n+n'\neq 0$.

Preferably, an aromatic polyamine compound in which m+m' is 2 or 3 is used.

More preferably, $Ar^1$ and $Ar^2$ independently are a substituted or non-substituted phenyl- or phenylene-structure having 6 to 20 carbon atoms.

Examples of $R^3$, $R^4$, and $R^5$ can include, but not limited to, linear hydrocarbon groups such as methylene, dimethylene, trimethylene, tetramethylene, pentamethylene, hexamethylene or octamethylene; cyclichydrocarbon groups such as cyclopentyl, cyclohexyl, cycloheptyl, cyclooctyl, bis(cyclohexyl), or alkyl-substituted cyclooctayl; alkyl-substituted cyclohydrocarbon groups such as methylcyclopentyl, ethylcyclopentyl, methylcyclohexyl, ethylcyclohexyl, propylcyclohexyl, butylcyclohexyl, pentylcyclohexyl or hexylcyclohexyl; dialkyl-substituted cyclohydrocarbon groups such as dimethylcyclohexyl, diethylcyclohexyl; trialkyl-substituted cyclohydrocarbon groups such as 1,5,5-trimethylcyclohexyl, 1,5,5-triethylcyclohexyl, 1,5,5-tripropylcyclohexyl or 1,5,5-tributylcyclohexyl; monoalkyl-substituted phenyl such as toluene, ethylphenyl or propyl phenyl; dialkyl-substituted phenylss such as xylene, diethyl phenyl or dipropylphenyl; and aromatic groups such as diphenylalkyl or benzene. In particular, hexamethylene, phenylene, diphenylmethane, toluene, cyclohexane, xylenyl, methylcyclohexane, isophorone and dicyclohexylmethane are used preferably.

Examples of such polyamine compounds can include, but not limited to, aromatic diamines such as 1,4-phenylene diamine, toluene diamines (2,4-, 2,6-, or mixture of both), 4,4'-methylene dianiline, methylene diailines (mixtures of 2,2',2,4'- and 4,4'-MDA isomers) or 4,4'-isopropylidene dianiline. Preferably, an aromatic diamine such as 4,4'-methylene dianiline is used.

The carboxylic acid usable for the processes as the carbonylation catalyst to form biscarbamates is selected from the group consisting of the compounds represented by the following formula (3):

$$R^6-COOH \quad (3)$$

in which $R^6$ represents an alkyl, cycloalkyl, aryl, heterocyclic group or combinations of any the above.

$R^6$ can be selected from the groups consisting of:
(1) alkyl having 2 to 17 carbon atoms, for example, acetic, butyl, tert-butyl and 1-methylcyclohexyl groups;
(2) cycloalkyl having 5 to 16 carbon atoms, for example, cyclohexyl group;
(3) aryl having 7 to 17 carbon atoms, for example, phenyl (benzoic) and naphthyl; and
(4) heterocyclic group having 5 to 16 carbon atoms, for example, furyl, thienyl, and pyridyl.

The carboxylic acid preferably has pKa of about 3.5 to about 5.0, preferably about 4.0 to about 5.0, more preferably about 4.0 to about 4.7. The carboxylic acid used in the process of the present invention preferably is selected from benzoic acid, p-tert-butylbenzoic acid, p-anisic acid, isobutyric acid, propionic acid, butyric acid, and pivalic acid. More preferably, benzoic acid is used.

According to the present invention, the reaction temperature of the process of producing the aryl carbamate is variable in response to the types of the material compounds and the reaction medium, and is in the range from about 20° C. to 100° C., and preferably 40° C. to 80° C., and preferably 40° C. to 75° C. and more preferably 40° C. to 60° C. in the presence of a tertiary amine.

According to the present invention, a tertiary amine is added to the reaction as a co-catalyst with carboxylic acid to facilitate the production of the aryl carbamate. In doing so, the added tertiary amines can accelerate formation of the aryl carbamate at a temperature of about 40° C. to about 75° C. More convincingly, tertiary amine-carboxylic acid co-catalysts promoting carbonylation for the production of the aryl carbamate is found to give a yield of the aryl carbamate of up to 99% at mild temperature of about 40° C. to about 75° C. in 16 hours as indicated in Table 5.

The tertiary amine for use as co-carbonylation catalyst in the process of the present invention is selected from pyridine, alkylpyridine, dimethylamino pyridine, 1,4-diazabicycle[2,2,2]octane, triethylamine, trialkylamine, 5-alkyl-1,5,7-triamino-bicycledodecane-5-ene, 1,5-diamino[4.3.0]-5-nonene, 1,8,-diaminobicycle[5,4,0]undec-7-ene, and N,N,N,N,N-pentaalkyl-guanidine. Among the tertiary amines, pyridine, 1,4-diazabicycle[2,2,2]octane (TEDA), and triethylamine are preferred.

The reaction pressure of making biscarbamates may be the ambient atmospheric pressure, an increased pressure or reduced pressure, and thus there is no specific limitation to the reaction pressure. Preferably, the reaction is carried out while stirring the reaction mixture. However, the stirring is not always necessary.

A reaction medium enhancing the operational efficiency of the reaction is preferably used. The reaction medium usable for the process of the present invention is not limited to specific groups of the compounds, as long as the reaction medium is not-reactive or scantly reactive to the diaryl carbonate and the amine compounds used as starting materials, to the resulted carbamate, to the carboxylic acid, and to the tertiary amine.

The reaction medium is preferably used, for example, in an amount of 50 parts by weight or less, more preferably 20 parts by weight or less, still more preferably 10 parts by weight or less, per part by weight of the diaryl carbonate. In the case where an aromatic amine (or secondary amine) is used, the reaction medium is preferably employed in an amount of, for example, 10 parts by weight or less, more preferably, 5 parts by weight or less, per part by weight of the diaryl carbonate. Also, the reaction medium may consist of only one compound or of a mixture of two or more compounds.

As a reaction medium usable for the process of producing an aryl carbamate of the present invention, for example, can include, but not limited to aliphatic alcohols (for example, methanol and ethanol); aliphatic hydrocarbons (for example, hexane, heptane, petroleum ether, cyclopentane, and cyclododecane); aromatic hydrocarbons (for example, benzene, toluene, and xylene); ethers (for example, diethylehter and diphenylether); nitriles (for example, acetonitrile and benzonitrile); nitriles (for example, acetonitrile and adiponitrile); aliphatic halogenated hydrocarbons (for example, methylene chloride and chloroform); amides (for example, N,N-dimethylformamide and N,N-dimethylacetamide); nitro compounds (for example, nitromethane and nitrobenzene); phenol compounds (for example, phenol, cresole, and xylenol); and N-methylpyrrolidinone, N,N-dimethylimidazolidinone, and dimethylsulfoxide.

Among the above-mentioned reaction mediums, aliphatic hydrocarbons (for example, hexane, heptane, petroleum ether, cyclopentane, and cyclododecane) and aromatic hydrocarbons (for example, benzene, toluene, and xylene) are preferably used; and aromatic hydrocarbons such as toluene and xylene are more preferably used.

In one embodiment of the process of producing a aryl carbamate of the present invention, a molar ratio of the aromatic polyamine compound to the diaryl carbonate of 1:1.5 to 1:8.5 is used; preferably a molar ratio of the aromatic polyamine compound to the diaryl carbonate of 1:2.5 to 1:7.5 is used; and more preferably a molar ratio of the aromatic polyamine compound to the diaryl carbonate of 1:3.5 to 1:6.5 is used.

In one embodiment of the process of producing a aryl carbamate of the present invention, a molar ratio of the aromatic polyamine compound to the carboxylic acid of 1:0.025 to 1:0.45 is used; preferably a molar ratio of the aromatic polyamine compound to the carboxylic acid of 1:0.035 to 1:0.35 is used; and more preferably a molar ratio of the aromatic polyamine compound to the carboxylic acid of 1:0.045 to 1:0.25 is used.

In one embodiment of the process of producing a aryl carbamate of the present invention, a molar ratio of the aromatic polyamine compound (to be carbonylated) to the tertiary amine catalyst (used for promoting carbonylation) of 1:0.0003 to 1:0.007 is used; preferably a molar ratio of the aromatic polyamine compound (to be carbonylated) to the tertiary amine (used for promoting carbonylation) of 1:0.0004 to 1:0.006 is used; and more preferably a molar ratio of the aromatic polyamine compound (to be carbonylated) to the tertiary amine (used for promoting carbonylation) of 1:0.0005 to 1:0.005 is used.

According to the process of producing diaryl carbamates of the present invention, after the reaction is completed, the target aryl carbamate is precipitated and collected from the reaction mixture. In the collection step, the temperature of the reaction mixture is cooled to room temperature, or controlled to about 40° C. or less, preferably about 40° C. to about −30° C., more preferably about 30° C. to about −25° C. to precipitate the aryl carbamate from the reaction mixture, and the precipitated aryl carbamate is isolated and collected by filtration or centrifugal separation.

A treatment can be applied to the resulted reaction mixture, to isolate and collect the aryl carbamate. For example, the reaction medium, the carboxylic acid, and the phenol compound in the reaction mixture can be isolated from the reaction mixture by distillation, and the remaining solid substance is directly collected, or the solid substance is washed with a solvent, or recrystallized, to isolate and collect the aryl carbamate.

If necessary, the mother liquid after filtration of aryl carbamate can be subjected to another treatment mentioned above to advantageously recover more the aryl carbamate remaining in the mother liquid.

If necessary, the aryl carbamate can be further refined by applying recrystallization.

After the filtration or centrifugal separation, the mother liquid can be re-used for the process of producing a aryl carbamate of the present invention, by, after optionally removing the phenol compounds produced as by-products and the reaction medium from the mother liquid by distillation or washing with a solvent (for example, toluene), and adding the diary carbonate, amine compounds, and carboxylic acid in necessary amounts to the mother liquid.

The solvent usable for the above-mentioned recrystallization includes, but not limited to, aliphatic hydrocarbons (for example, pentane and cyclododecane); aromatic hydrocarbons (for example, benzene, toluene, and xylene); aliphatic alcohols (for example, ethanol and n-butyl alcohol); ethers (for example, di-n-propylether); esters (for example, ethyl acetate and isobutyl acetate, and cyclohexyl acetate); and ketones (for example, methylisobutylketone and cyclohexanone).

Reference is now made to FIG. 1. In FIG. 1, curve (A) represents a carbonylation of 4,4'-DP-MDC carried out without tertiary amine added; curve (B) represents a carbonylation of 4,4'-DP-MDC carried out with a tertiary amine (TEDA) added and for 2 hours; and curve (C) represents a carbonylation of 4,4'-DP-MDC carried out with a tertiary amine added and for 5 hours. The differences of the absorption peaks at 1760 cm$^{-1}$ and 1680 cm$^{-1}$ show that a carbonylation of 4,4'-DP-MDC carried out with a tertiary amine added is more facile and complete. Therefore, the addition of a tertiary amine can improve the production of aryl carbamate.

Production of Isocyanate

According to the present invention, an isocyanate is produced by applying a thermo decomposition reaction to the aryl carbamate obtained according to the present invention in the presence of an inhibitor and a non-polar solvent. The use of an inhibitor specified in this invention together with a non-polar solvent are found to speed up the removal of phenol generated in heating and in the meantime slowing down the formation of carbodiimide by-products from dimerization of isocyanate product. Both of these two effects are essential in securing high yield formation of MDI from its biscarbamate in the thermolysis process.

The thermal decomposition reaction in the present embodiment is a reaction in which a corresponding isocyanate (MDI) and aromatic hydroxyl compound (phenol) are formed from the aryl carbamate and separated in the same step.

The reaction temperature is generally within a range of about 100 to about 300° C., preferably within a range of from about 150 to about 250° C., and more preferably with a range of from about 190 to about 230° C. The reaction pressure can be reduced pressure, normal pressure or increased pressure, in which normal pressure is preferred.

There are no particular limitations on the reaction time. The reaction time is generally from 0.001 to 100 hours, preferably from 0.005 to 50 hours, and more preferably from 1 to 3 hours.

There are no particular limitations on the molar ratio of the inhibitor to the aryl carbamate in the process of the present invention. In one embodiment of the process of producing an isocynate of the present invention, a molar ratio of the inhibitor to the aryl carbamate of 1:0.003 to 1:0.07 is used; preferably a molar ratio of the inhibitor to the aryl carbamate of 1:0.004 to 1:0.06 is used; and more preferably a molar ratio of the inhibitor to the aryl carbamate of 1:0.005 to 1:0.05 is used.

The inhibitors used in the process according to the present invention are any acid chlorides. Preferably, the inhibitors are those with boiling points of well over 180° C. so that they will not be distilled over during the carbamate thermo process, which can include but not limited to any aliphatic, aliphatic substituted phenyl or aromatic carboxylic acid chlorides with b.p. over 180° C., such as benzoyl chloride.

The non-polar solvent used in the process of producing isocyanate according to the present invention includes but not limited to any non-polar aliphatic hydrocarbon compounds, in particular any non-polar aliphatic hydrocarbon compounds with boiling points of >180° C. and above, any petroleum distillates with boiling points of >180° C., and the mixtures thereof, such as n-dodecane or cyclohexylbenzene.

Production of Polyurea

According to the present invention, a polyurea can be prepared directly from the aryl carbamate with an amine compound or mixtures thereof. Polyurea is produced by reacting the aryl carbamate obtained by the process mentioned above with an amine compound or mixtures thereof in the presence of a polar solvent.

The amine compound usable in preparing the polyurea according to the present invention is selected from the group consisting of short and long-chained diamines of aliphatic or aromatic, including ether diamines such as 1,8-diamino-3,6-dioxaoctane and long chained polyether diamines such as polyethoxylated or polypropoxylated diamines (D-2000); aliphatic diamines such as 1,6-hexanediamine (1,6-HDA), 4,4'-methylenedianiline (MDA); cyclic aliphatic diamines such as isophorone diamines (IPDA) or $H_{12}$MDA (hydrogenated MDA); aromatic diamines such as 4,4'-methylenedianiline (MDA); and long chained polyether diamines such as polyethoxylated or polypropoxylated diamines.

The preferred polar solvent usable for the trans-ureation process of making polyurea according to the present invention includes dimethylacetamide (DMAc), N-methyl-pyrolidone (NMP), dimethyl sulfoxide (DMSO) or tetramethylene sulfone (TMS). Preferably, DMSO or TMS is used.

TMS (b.p.=289° C.) is the most preferred because we could carry out the trans-ureation polymerization at a higher temperature (140° C.) and in the meantime applied vacuum to the reaction mixtures. By doing so simultaneously, phenol removal from the mixture was found to greatly facilitate the forward reaction that speed up the rate of polymerization resulting in high polymer formation in short time. For example, aromatic diamine (such as MDA) and cyclic diamine (such as $H_{12}$MDA) which failed to make polyurea elastomeric films in DMSO at 80° C., because of in-sufficient high molecular built-up, have no problem in getting polyurea films by the process of the present invention using TMS.

The reaction temperature is generally within a range of about 60 to about 200° C., preferably within a range of from about 60 to about 160° C., and more preferably within a range of from about 60 to about 100° C. The reaction pressure can be reduced pressure, normal pressure or high pressure, in which normal pressure is preferred.

There are no particular limitations on the reaction time. The reaction time is generally from 0.001 to 100 hours, preferably from 0.005 to 50 hours, and more preferably from 0.1 to 10 hours.

Having generally described this invention, a further understanding can be obtained by reference to certain specific examples which are provided herein for purposes of illustration only and are not intended to be limiting unless otherwise specified.

Comparative Example 1

Synthesis of 4,4'-methylenediphenylene biscarbamate 4,4'-methylenedianiline (MDA, 19.8 g, 100 mmole), diphenyl carbonate (DPC, 128.4 g, 600 mmole), and catalyst benzoic acid (2.44 g, 20 mmole) were added into a 500 ml three-neck bottle containing 150 ml of toluene. The mixture was stirred with a magnetic stir bar and heated to 80° C. with an oil bath. One neck of the bottle was equipped with a thermometer and charged with nitrogen, and another neck was connected to a condenser charged with water of which the upper end was connected with oil seal. The reaction was carried out for 16 hours. The reaction ended when the TLC analysis indicated the absence of 4,4'-methylenedianiline and the mono-carbamate intermediate.

After the reaction was completed, the reaction mixture was continuous stirred and the temperature was slowly lowered to room temperature. It was observed that white crystalline products were precipitated. Suction filtration was then applied to obtain the products. The obtained products was washed by toluene (50 ml), filtered, and dried in a vacuum oven at 80° C. for 6 hours. Opalescence solid crystalline products (43.1 g) were collected ($^1$H-NMR (200 MHz, $d_6$-Aceton) δ (ppm): 3.9 (s, 2H, -PhCH$_2$Ph-), 7.17-7.55 (m, 18H, -Ph- and —OPh-), 9.1 (br s, 2H, —NH—)). The yield is 98.5% and the melting point is 191 to 192° C.

Example 1

Synthesis of 4,4'-methylenediphenylene biscarbamates with Different Carboxylic Acids The same procedures, quantity of reagents, and analysis in Comparative Example 1 were carried out, except that benzoic acid was replaced by other carboxylic acids as shown in Table 1. The acid candidates being tested included both aliphatic and aromatic carboxylic acids with their pKa values spreading between 0.2 and 5.0. The screened candidates and synthesis condition are summarized in Table 1. The result of the 4,4'-DP-MDC yield curve plotted against pKa values is shown in FIG. 1. and it indicates that carboxylic acid with pKa of 4.0 to 5.0 out-performs the rest. When carboxylic acids with pKas of 4.4-5.0 were used in our screening study, the yields of 4,4'-DP-MDC are all greater than 93%, but a slight declining trend of biscarbamate yields could be discerned as indicated in FIG. 1. This screening result supports that benzoic acid has been the best choice so far. Even if the concentration of benzoic acid was reduced to ¼ of the optimal concentration, high yield (92%) of 4,4'-DP-MDC could still be isolated (see FIG. 2. and Table 2.). The effect of diphenyl carbonate concentrations on the yields of 4,4'-DP-MDC has also been investigated, and the decrease of DPC concentrations shows a negative impact on yield of 4,4'-DP-MDC as indicated in FIG. 3. and Table 3. However, about 90% yields of biscarbamate still could be achieved when the concentration of DPC was reduced 50% from its original optimal concentration.

It is found from the below table that benzoic acid can produce higher yield and therefore is the preferred acid among the choices of acids.

TABLE 1

| Carboxylic acid | pKa | Yield (%) of biscarbamate/urea for Molar ratio of MDA:DPC:Acid = 1:6:0.2 | Yield (%) of biscarbamate/urea for Molar ratio of MDA:DPC:Acid = 1:6:0.05 |
|---|---|---|---|
| Trifluoro acetic acid | 0.23 | 38/1.62 | 38/0.35 |
| Dichloro acetic acid | 1.25 | 70/2.55 | 67/0.37 |
| p-Nitrobenzoic acid | 3.41 | 100/0.66 | 93/0.10 |
| Formic acid | 3.77 | 75/0.00 | 47/0.22 |
| Benzoic acid | 4.21 | 98.5/0.08 | 92/0.62 |
| p-tert-Butylbenzoic Acid | 4.40 | 96/1.28 | 87/0.86 |
| p-Anisic acid | 4.47 | 99/0.56 | 88/0.77 |
| Isobutyric acid | 4.86 | 93/1.09 | 85/0.00 |
| Propionic acid | 4.87 | 97/0.47 | 86/0.46 |
| Pivalic acid | 5.0 | 95/0.05 | 85/0.53 |

$^a$pKa value = −log (acid dissociation constant).
$^b$based on molar ratio of 4,4'-MDA:DPC:carboxylic acid = 1:6:0.2.
$^c$Calculated by $^1$H-NMR analysis.

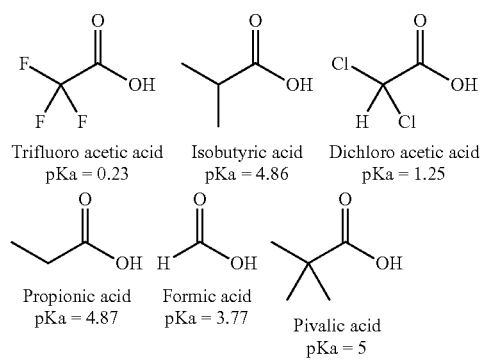

Aliphatic Carboxylic Acid

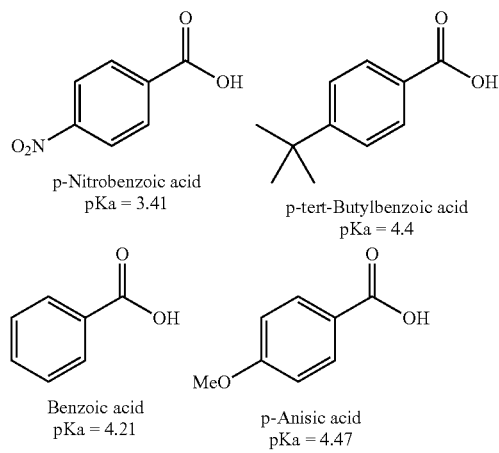

Aromatic Carboxylic Acid

Example 2

Synthesis of 4,4'-methylenediphenylene biscarbamates with Different Amounts of Benzoic Acid The same procedures and analysis in Comparative Example 1 were carried out, except that the amount of benzoic acid was changed as shown in Table 2. It is found from the below table that the yield of 4,4'-methylenediphenylene biscarbamates can still maintain at least 90% when the amount of benzoic acid continues reducing to one-twenty of moles of MDA.

TABLE 2

| Carboxylic acid | Molar ratio of MDA:DPC:Acid | Weight of Carboxylic acid | Yield (%) of biscarbamate | Yield (%) of urea |
|---|---|---|---|---|
| Benzoic acid | 1:6:0.2 | 2.44 g | 98.5 | 0.08 |
| Benzoic acid | 1:6:0.1 | 1.22 g | 95 | 0.01 |
| Benzoic acid | 1:6:0.05 | 0.61 g | 92 | 0.62 |
| Benzoic acid | 1:6:0.025 | 0.305 g | 83 | 0.47 |
| Benzoic acid | 1:6:0.0125 | 0.1625 g | 66 | 0.58 |

Example 3

Synthesis of 4,4'-methylenediphenylene biscarbamates with Different Amounts of Diphenyl Carbonate The same procedures and analysis in Comparative Example 1 were carried out, except the amount of diphenyl carbonate as shown in Table 3. It is found from the below table that the yield of 4,4'-methylenediphenylene biscarbamates can still maintain at least 90% when the amount of diphenyl carbonate continues reducing to 3 times of moles of MDA.

TABLE 3

| Molar ratio of MDA:DPC:Acid | Yield (%) of biscarbamate | Weight of diphenyl carbonate | Yield (%) of urea |
|---|---|---|---|
| 1:6:0.2 | 98.5 | 128.4 g | 0.08 |
| 1:4:0.2 | 95 | 85.6 g | 1.01 |
| 1:3:0.2 | 90 | 64.2 g | 0.42 |
| 1:2.5:0.2 | 83 | 53.5 g | 1.33 |
| 1:2:0.2 | 74 | 42.4 g | 1.18 |

Example 4

Synthesis of 4,4'-methylenediphenylene biscarbamates with Different Amounts of Solvent (Toluene)

The same procedures and analysis in Comparative Example 1 were carried out, except the amount of solvent (toluene) as shown in Table 4. It is found from the below table that 150 ml to 200 ml of toluene with 19.8 g of MDA is preferred.

TABLE 4

| Amount of solvent used | Yield (%) of biscarbamate | Yield (%) of urea |
|---|---|---|
| 100 ml Toluene used | 95 | 0.53 |
| 150 ml Toluene used | 98.5 | 0.08 |

TABLE 4-continued

| Amount of solvent used | Yield (%) of biscarbamate | Yield (%) of urea |
|---|---|---|
| 200 ml Toluene used | 96 | 0.71 |
| 250 ml Toluene used | 94 | 0.38 |

Example 5

Synthesis of 4,4'-methylenediphenylene biscarbamate with Benzoic Acid and Pyridine as Co-Catalysts 4,4'-methylenedianiline (MDA, 19.8 g, 100 mmole), diphenyl carbonate (DPC, 128.4 g, 600 mmole), and catalysts benzoic acid (2.44 g, 20 mmole) and pyridine (0.07 g, 0.9 mmole) were added into a 500 ml three-neck bottle containing 150 ml of toluene. The mixture was stirred with a magnetic stirbar and heated to 65° C. with an oil bath. One neck of the bottle was equipped with a thermometer and charged with nitrogen, and another neck was connected to a condenser charged with water of which the upper end was connected with oil seal. The reaction was carried out for 16 hours. The reaction ended when the TLC analysis indicated the absence of 4,4'-methylenedianiline and mono-carbamate intermediate.

After the reaction was completed, the reaction mixture was continuous stirred and the temperature was slowly lowered to room temperature. It was observed that white crystalline products were precipitated. Suction filtration was then applied to obtain the products. The obtained products was washed by toluene (50 ml), filtered, and dried in a vacuum oven at 80° C. for 6 hours. Opalescence solid crystalline products were collected. The yield is 97%, the yield of urea is 1.39%, and the melting point is 191 to 192° C.

It is found that the tertiary amine pyridine can effectively lower the reaction temperature of the carbonylation process.

Comparative Example 2

Synthesis of 4,4'-methylenediphenylene biscarbamate with Benzoic Acid as the Only Catalyst at 45° C.

4,4'-methylenedianiline (MDA, 19.8 g, 100 mmole), diphenyl carbonate (DPC, 128.4 g, 600 mmole), and catalyst benzoic acid (2.44 g, 20 mmole) were added into a 500 ml three-neck bottle containing 150 ml of toluene. The mixture was stirred with a magnetic stirbar and heated to 45° C. with an oil bath. One neck of the bottle was equipped with a thermometer and charged with nitrogen, and another neck was connected to a condenser charged with water of which the upper end was connected with oil seal. The reaction was carried out for 16 hours. The reaction ended when the TLC analysis indicated the absence of 4,4'-methylenedianiline.

After the reaction was completed, the reaction mixture was continuous stirred and the temperature was slowly lowered to room temperature. It was observed that white crystalline products were precipitated. Suction filtration was then applied to obtain the products. The obtained products was washed by toluene (50 ml), filtered, dried in a vacuum oven at 80° C. for 6 hours. Opalescence solid crystalline products were collected. The yield is 65%, the yield of urea is 1.06%, and the melting point is 191 to 192° C.

Example 6

Synthesis of 4,4'-methylenediphenylene biscarbamate with Benzoic Acid and 1,4-diazabicycle[2,2,2]octane (TEDA) as Catalysts at 45° C.

4,4'-methylenedianiline (MDA, 19.8 g, 100 mmole), diphenyl carbonate (DPC, 128.4 g, 600 mmole), and catalysts benzoic acid (2.44 g, 20 mmole) and 1,4-diazabicycle[2,2,2]octane (0.1 g, 0.9 mmole) were added into a 500 ml three-neck bottle containing 150 ml of toluene. The mixture was stirred with a magnetic stirbar and heated to 45° C. with an oil bath. One neck of the bottle was equipped with a thermometer and charged with nitrogen, and another neck was connected to a condenser charged with water of which the upper end was connected to an oil seal. The reaction was carried out for 16 hours. The reaction ended when the TLC analysis indicated the absence of 4,4'-methylenedianiline.

After the reaction was complete, the reaction mixture was stirred and the temperature was slowly lowered to room temperature. It was observed that white crystalline products were precipitated. Suction filtration was then applied to obtain the products. After the filtered solution was keep static for one day, a second filtration was processed to obtain the secondary product. The obtained products were cleaned with 50 ml and 20 ml toluene respectively, filtered, and then dried in a vacuum oven at 80° C. for 6 hours. Opalescence solid crystalline products were collected. The yield was 99%, the urea yield is 0.15% and the melting point is 191 to 192° C.

It was found that 1,4-diazabicycle[2,2,2]octane as the co-catalyst with benzoic acid can effectively reduce the reaction temperature of the carbonylation process.

The results of the above Comparative Example 2, Example 5, and Example 6 are shown in the following Table 5.

TABLE 5

| | Molar Ratio | | | |
|---|---|---|---|---|
| | Comparative Example 1 MDA:DPC:Acid = 1:6:0.2 | Comparative Example 2 MDA:DPC:Acid = 1:6:0.2 | Example 5 MDA:DPC:Acid:3°-Amine = 1:6:0.2:0.009 | Example 6 MDA:DPC:Acid:3°-Amine = 1:6:0.2:0.009 |
| Co-catalyst | None | None | Pyridine/0.07 g | TEDA/0.1 g |
| Time | 16 hr | 16 hr | 16 hr | 16 hr |
| Temp. | 80° C. | 45° C. | 65° C. | 45° C. |
| Yield (%) of biscarbamate | 98.5 | 65 | 97 | 99 |
| Yield (%) of urea | NA | 1.06 | 1.39 | 0.15 |

It is found from the above results that tertiary amine as the co-catalyst with benzoic acid can effectively facilitate the reaction at ambient temperature to 65° C., preferably about 45° C. to 65° C. and improve the yield.

Example 7

Reuse of Diphenyl Carbonate and Benzoic Acid after Removing the Byproduct Phenol by Cleaning with Toluene The filtered solution obtained by suction filtration process in Comparative Example 1 was recycled by first recycling all 145 ml toluene under reduced pressure concentration. The recycle proportion is 72.5%. Then, the precipitated solid powders were applied with suction filtration and then washed with 100 ml toluene, and after the filtration, were charged to a 500 ml three-neck bottle, with 4,4'-methylenedianiline (19.8 g, 100 mmole), diphenyl carbonate (64.2 g, 300 mmole), and catalyst benzoic acid (1.22 g, 10 mmole) and solvent toluene (150 ml). The mixture was stirred with a magnetic stirbar and heated to 80° C. with an oil bath. One neck of the bottle was equipped with a thermometer and charged with nitrogen, and another neck was connected to a condenser charged with water of which the upper end was connected with oil seal. The reaction was carried out for 16 hours. The reaction ended when the TLC analysis indicated the absence of 4,4'-methylenedianiline.

After the reaction was complete, the reaction mixture was continuously stirred and the temperature was slowly lowered to room temperature. It was observed that white crystalline products were precipitated. Suction filtration was then applied to obtain the products. The obtained products was washed with toluene (50 ml), filtered, and dried in a vacuum oven at 80° C. for 6 hours. Opalescence solid crystalline products were collected. The yield was 91%, the urea yield is 0.42% and the melting point is 191 to 192° C.

Example 8

Reuse of Diphenyl Carbonate and Benzoic Acid after Removing the Byproduct Phenol by Distillation The filtered solution obtained by suction filtration process in Comparative Example 1 was recycled by first recycling all 145 ml toluene under reduced pressure concentration. The recycle proportion is 71.5%. Then, the precipitated solid powders were applied with reduced pressure distillation at 100° C. for one hour to remove phenol and then charged to a 500 ml three-neck bottle, with fresh 4,4'-methylenedianiline (19.8 g, 100 mmole), diphenyl carbonate (64.2 g, 300 mmole), and catalyst benzoic acid (1.22 g, 10 mmole) and solvent toluene (150 ml). The mixture was stirred with a magnetic stirbar and heated to 80° C. with an oil bath. One neck of the bottle was equipped with a thermometer and charged with nitrogen, and another neck was connected to a condenser charged with water of which the upper end was connected with oil seal. The reaction was carried out for 16 hours. The reaction ended when the TLC analysis indicated the absence of 4,4'-methylenedianiline.

After the reaction was complete, the reaction mixture was continuously stirred and the temperature was slowly lowered to room temperature. It was observed that white crystalline products were precipitated. Suction filtration was then applied to obtain the products. The obtained products was washed with toluene (50 ml), filtered, and dried in a vacuum oven at 80° C. for 6 hours. Opalescence solid crystalline products were collected. The yield was 96%, the urea yield is 0.08% and the melting point is 191 to 192° C.

Comparative Example 3

Pyrolysis of 4,4'-methylene diphenyl dicarbamate in the Presence of High Polar Solvent Dimethyl Sulfoxide (DMSO)

4,4'-methylene diphenyl dicarbamate (38 g, 86.8 mmole) and inhibitor benzoyl chloride (0.09 g, 0.6 mmole) were charged to 500 ml three-neck bottle containing solvent DMSO (150 ml). The mixture was stirred with a magnetic stirbar and heated to 180° C. with an oil bath. One neck of the bottle was equipped with a thermometer and charged with nitrogen, and another neck was connected to a divide tube which was further connected to a condenser to charge with cold water. The upper end of the condenser was connected to a grease seal. The progress of the reaction was monitored by FT-IR. The disappearance of the absorption peak at 1740 $cm^{-1}$ indicates that the conversion of carbamate was complete (at 1.5 hours), and the disappearance after reappearance of the absorption peak at 2265 $cm^{-1}$ indicates that isocyanate generated in DMSO solution is consumed. In another words, the isocyanate product cannot undergo survive in the high polar solvent.

Comparative Example 4

Pyrolysis of 4,4'-methylene diphenyl dicarbamate in the Presence of Tetramethylene Sulfone (TMS)

4,4'-methylene diphenyl dicarbamate (38 g, 86.8 mmole) and inhibitor benzoyl chloride (0.09 g, 0.6 mmole) were charged to 500 ml three-neck bottle containing solvent TMS (150 ml). The mixture was stirred with a magnetic stirbar and heated to 200° C. with an oil bath. One neck of the bottle was equipped with a thermometer and charged with nitrogen, and another neck was connected to a divide tube which was further connected to a condenser to charge with cold water. The upper end of the condenser was connected to a grease seal. The reaction temperature was 200° C. The progress of the reaction was monitored by FT-IR. It was observed that the absorption peaks at 1744 $cm^{-1}$ and the absorption peak at 3323 $cm^{-1}$ were not completely disappeared at 2 hours, and the new absorption peak at 2274 $cm^{-1}$ did not further develop. Therefore, it was determined that the pyrolysis was not complete in polar solvent.

Example 9

Pyrolysis of 4,4'-methylene diphenyl dicarbamate in the Presence of Non Polar Solvent n-dodecane and Conversion of 4,4'-methylene diphenylene diisocyanate with Methanol 4,4'-methylene diphenyl dicarbamate (38 g, 86.8 mmole) and inhibitor benzoyl chloride (0.09 g, 0.6 mmole) were charged to 500 ml three-neck bottle containing solvent n-dodecane (250 ml, 191.4 g). The mixture was stirred with a magnetic stirbar and heated to 210° C. with an oil bath. One neck of the bottle was equipped with a thermometer and charged with nitrogen, and another neck was connected to a divide tube which was further connected to a condenser to charge with cold water. The upper end of the condenser was connected to a grease seal. The reaction was carried out for 2.5 hours. The progress of the reaction was monitored by FT-IR. It was observed that the absorption peak at 1720 cm$^{-1}$ and the absorption peak at 3335 cm$^{-1}$ disappeared completely, and an absorption peak appeared at 2270 cm$^{-1}$. After part of n-dodecane (100 ml) and produced phenol (15.39 g) were retrieved from the divide tube, heating was stopped and the reaction ended.

After the reaction was complete, the reaction mixture was continuously stirred and the temperature was slowly lowered to room temperature, and the temperature is then raised to 80° C. to carry out reduced pressure distillation to distill the remaining solvent. Total 179.78 g n-dodecane was recycled. The remaining solution in the three-neck bottle was placed in a 250 ml three-neck bottle with solvent xylene (150 ml). The mixture was stirred with a magnetic stirbar. One neck of the bottle was equipped with a thermometer and charged with nitrogen and another neck was connected to a condenser to charge with cold water. The upper end of the condenser was connected to a grease seal. The last neck was connected to a feed tube filled with methanol (9.6 g, 300 mmole), which was slowly dropped into the three-neck bottle at about a rate of 1 drop/sec. The reaction temperature was 70° C. The reaction was carried out for 2 hours. The progress of the reaction was monitored by FT-IR. After the absorption peak at 2270 cm$^{-1}$ disappeared, the heating was stopped and the reaction ended.

After the reaction ended, the reaction mixture was continuously stirred and the temperature was slowly lowered to room temperature. It was observed that white crystalline products were precipitated. Suction filtration was then applied to obtain the products. The obtained products were washed with 50 ml xylene, filtered, and then dried in a vacuum oven at 110° C. for 6 hours. Opalescence solid crystalline products were collected. This result indicated indirectly that the yield of MDI was at least 85% based on the derivative formed in the solution. The recycled yield of phenol and n-dodecane was 95% and 95% respectively.

It is found from this example that when the pyrolysis of 4,4'-methylene diphenyl dicarbamate is carried out in the presence of non-polar solvent n-dodecane, the highest yield of 4,4'-methylene diphenylene di isocyanate (4,4'-MDI) is 85%.

Example 10

Pyrolysis of 4,4'-methylene diphenyl dicarbamate in the Presence of Non Polar Solvent n-dodecane and Preparation of 4,4'-methylene diphenylene diisocyanate by Distillation 4,4'-methylene diphenyl dicarbamate (38 g, 86.8 mmole) and inhibitor benzoyl chloride (0.09 g, 0.6 mmole) were charged to 500 ml three-neck bottle with solvent n-dodecane (250 ml, 189.19 g). The mixture was stirred with a magnetic stirbar and heated to 210° C. with an oil bath. One neck of the bottle was equipped with a thermometer and charged with nitrogen, and another neck was connected to a divide tube which was further connected to a condenser to charge with cold water. The upper end of the condenser was connected to a grease seal. The reaction was carried out for 2.5 hours. The progress of the reaction was monitored by FT-IR. It was observed that the absorption peak at 1720 cm$^{-1}$ and the absorption peak at 3335 cm$^{-1}$ disappeared completely, and the absorption peak appeared at 2270 cm$^{-1}$. After part of n-dodecane (100 ml) and produced phenol (15.63 g) was retrieved from the divide tube, the heating was stopped and the reaction ended.

After the reaction ended, the reaction mixture was continuously stirred and the temperature was slowly lowered to room temperature, and then raised to 80° C. again to carry out reduced pressure distillation to distill the remaining solvent. Total 179.7 g n-dodecane was recycled. The temperature was then raised to 170° C. to carry out reduced pressure distillation to obtain white crystalline products 4,41-methylene diphenylene diisocyanate (16.35 g). The yield was 75% and the recycle proportion is 88% (on the basis of the highest yield of 4,4'-MDI obtained in Example 10). The recycle proportion of phenol and n-dodecane is 95% and 95% respectively.

Although the recycle proportion of 4,4'-MDI is 88% at the laboratory distillation scale, it is believed that the initial product of 4,4'-MDI obtained by pyrolysis can be recycled at least 95% at the industry scale, that is the final yield of 4,4'-MDI is greater than about 80%.

Example 11

Pyrolysis of 4,4'-methylene diphenyl dicarbamate in the Presence of Non Polar Solvent n-dodecane and Preparation of 4,4'-methylene diphenylene diisocyanate by Crystallizing Process 4,4'-methylene diphenyl dicarbamate (38 g, 86.8 mmole) and inhibitor benzoyl chloride (0.09 g, 0.6 mmole) were charged to 500 ml three-neck bottle with solvent dodecane (250 ml, 188.12 g). The mixture was stirred with a magnetic stirbar and heated to 210° C. with an oil bath. One neck of the bottle was equipped with a thermometer and charged with nitrogen, and another neck was connected to a divide tube which was further connected to a condenser to charge with cold water. The upper end of the condenser was connected to a grease seal. The reaction was carried out for 2.5 hours. The progress of the reaction was monitored by FT-IR. It was observed that the absorption peak at 1720 cm$^{-1}$ and the absorption peak at 3335 cm$^{-1}$ disappeared completely, and the absorption peak appeared at 2270 cm$^{-1}$. After part of n-dodecane (100 ml) and produced phenol (15.41 g) was retrieved from the divide tube, the heating was stopped and the reaction ended.

After the reaction ended and the temperature was slowly lowered to room temperature, solution was connected in a 500 ml single-neck bottle and was kept static for 12 hours to ensure that the seed crystal forms completely, and which was then placed into the refrigerator at 10° C. for 6 hours. Suction filtration was then applied to obtain the crystalline and to recycle solvent n-dodecane (159.87 g). The obtained products were filtered, and then dried in a vacuum oven at 20° C. for one day to obtain white crystalline products 4,4'-methylene diphenylene diisocyanate (16.2 g). The yield was 75%. The recycle proportion was 88% (on the basis of the highest yield of 4,4'-MDI obtained in Example 10). The recycle proportion of phenol and n-dodecane was 95% and 85% respectively.

Example 12

Synthesis of Polyurea in TMS from 4,4'-methylene diphenyl dicarbamate

A 250 mL resin kettle equipped with a mechanical stirrer, thermometer, and nitrogen inlet and outlet was charged with 4,4'-methylene diphenyl dicarbamate (4,4'-DP-MDC, 5.79 g; 13.2 mmol), 1,6-hexanediamine (1,6-HDA, 0.95 g; 8.2 mmol), polyester diamine (PPG-DA-2000, Jeffamine D-2000, 10.0 g, 5.0 mmol) in TMS (66.96 g, solid content is set as 20%), the mixed solution was stirred at room temperature initially under atmospheric pressure. The relative molar ratio of 4,4'-DP-MDC/1,6-HDA/PPG-DA-2000 used in the preparation was 1:0.62:0.38. The reaction mixture was then heated to 90° C. for 1 hour followed by a subsequent of vacuum distillation (7×10−3 mmHg) at about 140° C. for 2 hours to drive off phenol from the mixture. After the completion of reaction, the TMS solution was dropped into 300 mL of water to precipitate the polyurea. The polymer was collected by filtration and then the product was dried in an oven at 140° C. for 3 hours and 90° C. for additional 5 hours to get 12.3 g. (86%) of polyurea. The product was cast into film in N-Methyl-2-pyrrolidinone (NMP) solution and then was characterized by GPC, TGA, DSC and measured its elongation and tensile strength.

As the above-mentioned examples clearly illustrates, the process of the present invention for producing an aryl carbamate can produce the aryl carbamate in a high yield under moderate conditions.

Also, in the process of the present invention, the resulted aryl carbamate can be easily isolated and collected from the reaction mixture liquid, refined, and for further reaction, for example, for production of isocynates or polyureas.

As the above-mentioned examples clearly illustrates, the process of the present invention can produce an isocynate effectively by the resulted aryl carbamate.

At 80° C., tetramethylene sulfone (TMS) behaves like DMSO and can also perform as the solvent for making polyurea in 90% through a similar trans-ureation. If the trans-ureation of 4,4'-DP-MDC was done in TMS under vacuum at 80-140° C., the removal of phenol became rapid and phenol could be recovered from the distillate for easy separation.

DMSO and TMS are not only excellent solvents to dissolve biscarbamates, but also they can serve as a good media for polyurea synthesis. However, trans-ureation in high-boiling-point TMS as the solvent has some advantages. For example, the separation of phenol from the solvent can be easily to overcome, and the TMS-modified method could recover and separate greater than 95% of TMS and 85% of phenol from TMS solution after the polymerization for reuse. Furthermore, trans-ureation of 4,4'-DP-MDC in TMS at 140° C. is capable of producing the highest molecular weight polyureas greater than 50,000 among different approaches consistently with varieties of diamines and diamine mixtures. Therefore, the new polyurea process based on 4,4'-DP-MDC in TMS is preferred.

According to the present invention, it becomes feasible to simplify the overall polyurea synthetic process bypassing the step of making MDI from biscarbamates altogether. In other words, the new polyurea process is a general, economical and effective green-process free from using toxic isocyanates and metal catalysts, and it has the potential for wide-spread applications.

It will be apparent to those skilled in the art that various modifications and variations can be made to the structure of the present invention without departing from the scope or spirit of the invention. In view of the foregoing, it is intended that the present invention covers modifications and variations of this invention provided they fall within the scope of the following claims and their equivalents.

We claim:

1. A process for producing an aryl carbamate, comprising reacting a diaryl carbonate with an aromatic polyamine compound at a temperature of about 40° C. to about 75° C. in the presence of a combination of at least one carboxylic acid and a tertiary amine as a catalyst, wherein the carboxylic acid and the tertiary amine are separate molecules.

2. The process of claim 1, wherein the diaryl carbonate is selected from the group consisting of diphenyl carbonate, bis(2-tolyl)carbonate, bis(4-chlorophenyl)carbonate, bis(4-nitrophenyl)carbonate, and bis(3,5-dimethoxyphenyl)carbonate.

3. The process of claim 1, wherein the aromatic polyamine compound is phenylene diamine, toluene diamine, 4,4'-methylene dianiline, or 4,4'-isopropylidene dianiline.

4. The process of claim 1, wherein the carboxylic acid is selected from the group consisting of benzoic acid, p-tert-butylbenzoic acid, p-anisic acid, isobutyric acid, propionic acid, butyric acid and pivalic acid.

5. The process of claim 1, wherein the tertiary amine for use as co-carbonylation catalyst is selected from the group consisting of pyridine, alkylpyridine, dimethylamino pyridine, 1,4-diazabicycle[2,2,2]octane, triethylamine, trialkylamine, 5-alkyl-1,5,7-triamino-bicycledodecane-5-ene, 1,5-diamino[4.3.0]-5-nonene, 1,8,-diaminobicycle[5,4,0]undec-7-ene, and N,N,N,N,N-pentaalkyl-guanidine.

6. The process of claim 1, wherein the diaryl carbonate is diphenyl carbonate, the aromatic polyamine compound is phenylene diamine, toluene diamine, or 4,4'-methylene dianiline, and the carboxylic acid is benzoic acid.

7. The process of claim 1, wherein the carboxylic acid has pKa of about 3.5 to about 5.5.

8. The process of claim 1, wherein the process is carried out at a temperature of about 40° C. to about 60° C.

9. A process for producing isocyanates, comprising preparing an aryl carbamate by reacting a diaryl carbonate with an aromatic polyamine compound at a temperature of about 40° C. to about 75° C. in the presence of at least one carboxylic acid and a tertiary amine as a carbonylation co-catalyst, wherein the carboxylic acid and the tertiary amine are separate molecules; and applying a thermo decomposition reaction to the aryl carbamate in the presence of an inhibitor and a non-polar solvent.

10. The process of claim 9, wherein the aromatic polyamine compound is phenylene diamine, toluene diamine, 4,4'-methylene dianiline, or 4,4'-isopropylidene dianiline.

11. The process of claim 9, wherein the inhibitor for isocyanate generation includes benzoyl chloride.

12. The process of claim 9, wherein the non-polar solvent for thermolysis of the aryl carbamate in formation of isocyanate is selected from the group consisting of n-dodecane and cyclohexylbenzene.

13. A process for producing a polyurea, comprising preparing an aryl carbamate by reacting a diaryl carbonate with an aromatic polyamine compound at a temperature of about 40° C. to about 75° C. in the presence of at least one carboxylic acid and a tertiary amine as a carbonylation co-catalyst, wherein the carboxylic acid and the tertiary amine are separate molecules; and reacting the aryl carbamate with an amine compound or mixtures thereof in the presence of a polar solvent.

14. The process of claim 13, wherein the amine compound or amine mixtures for polyurea synthesis are selected from the group consisting of 1,8-diamino-3,6-dioxaoctane, poly ether dimaines (D-2000), 1,6-hexanediamine (1,6-HDA), 4,4'-methylenedianiline (MDA), isophorone diamines (IPDA), and $H_{12}MDA$ (hydrogenated MDA).

15. The process of claim 13, wherein the long chained amine compounds are selected from the group consisting of polyethoxylated diamines and polypropoxylated diamines.

16. The process of claim 13, wherein the polar solvent is dimethyl sulfoxide (DMSO) or tetramethylene sulfone (TMS).

* * * * *